US005902786A

United States Patent [19]
Bregman

[11] Patent Number: 5,902,786
[45] Date of Patent: May 11, 1999

[54] TREATMENT OF BASAL CELL CARCINOMA WITH PRODUCT R, A PEPTIDE-NUCLEIC ACID PREPARATION

[75] Inventor: William Bregman, Miami Beach, Fla.

[73] Assignee: Advanced Viral Research Corp., Hallandale, Fla.

[21] Appl. No.: 08/835,792

[22] Filed: Apr. 15, 1997

[51] Int. Cl.$^6$ .......................... A61K 38/01; A61K 31/70
[52] U.S. Cl. ................... 514/2; 514/21; 514/44; 514/885
[58] Field of Search ................. 514/2, 44, 885, 514/21; 424/78.02, 78.03, 78.05, 78.08

[56] References Cited

U.S. PATENT DOCUMENTS

| | | | |
|---|---|---|---|
| 4,619,913 | 10/1986 | Luck et al. .................................. | 514/2 |
| 5,130,247 | 7/1992 | Kniskern et al. ..................... | 435/254.2 |
| 5,194,245 | 3/1993 | Carter ......................................... | 424/9 |

OTHER PUBLICATIONS

Ragni et al., Blood, 81:1889–1897, 1993.
Reynolds, Margaret R., Generalized Vaccinia, Symposium, pp. 5–6, 1960.
Kuckku, Morris E., Herpetic Diseases, Symposium, pp. 7–13, 1960.
Schaeffer, Oden A., Influenza, Symposium, pp. 15–21, 1960.
Seydel, Frank, Epidemic, Asian Influenza, Symposium, pp. 23–24, 1960.
Cooke, Stanford B., Upper Respiratory Viral Manifestations, Clinical Symposium on Viral Diseases Demonstrating the Anti–viral Biotic Properties of the Drug Reticulose (Symposium), Sep., 1960, Miami Beach, Florida, pp. 25–32.
Medoff, Lawrence R., Infectious Mononucleosis, Symposium, pp. 33–37, 1960.
Anderson, Robert H., Encephalitis, Symposium, pp. 39–52, 1960.
Plucinski, Stanisloff J., Suspected Viral Varieties, Symposium, pp. 53–59, 1960.
Kosaka, K. and Shimada, Y., Infectious Hepatitis, Symposium, pp. 61–74, 1960.
Anderson, Robert H. and Thompson, Ralph M., Treatment of Viral Syndrome with a Lipoprotein–Nucleic Acid Compound (Reticulose), A Report of Five Cases, Virginia Medical Monthly, 84: 347–353, 1957.
Reynolds, Margaret R., Generalized Vaccinia Successfully Treated With Lipoprotein–Nucleic Acid Complex (Reticulose), Archives of Pedratrics, 77:421–422, 1960.
Wegryn, Stanley P., Marks, Robert A. and Baugh, John R., Herpes Gestationis, A Report of 2 Cases, American Journal of Obstetrics and Gynecology, 79:812–814, 1960.
Catterall, R.A., Lumpur, Kuala, A New Treatment of Herpes Zoster, Vaccinia And Chicken Pox, J. Roy, Coll. Gen. Practit., 1970, 19, 182.
Chinnici, Angelo A., Reticulose in Treatment Aids patients, Personal Communication to William Bregman, Jul. 6, 1992.
Cott, Rafael A., Summary of 11 Cases of Viral Infections with Reticulose, Private Communication with Advance Viral Research Corp., 1989.
Cohen, Matthew, The Efficacy of a Peptide–Nucleic Acid Solution (Reticulose) for the Treatment of Hepatitis A and Hepatitis B—a Preliminary Controlled Human Clinical Trial, J. Roy Soc. Health, Dec., 1992, 266–270.
Mundschenk, David D., In Vitro Antiviral Activity of Reticulose vs Influenaz A, Personal Communication with William Bregman, May 1, 1990.
Resnick, Lionel, Anti–HIV in Vitro Activity of Two Samples of Peptide–nucleic Acid Solution, Personal Communication with Dr. Bernard Friedland, Dec. 22, 1989.
Friedland, Bernard, In Vitro Antiviral Activity of a Peptide–Nucleic Acid Solution Against the Human Immunodeficiency Virus and Influenza A Virus, J. Roy. Soc. Health, Oct. 1991, 170–171.
Brazier, Anne D., Method for in Vitro Antiviral Evaluation Human Immunodeficiency Virus (HIV), Personal Communication with Dr. Bernard Friedland, Oct. 4, 1989.
Behbehani, Abbas M., Haberman Sol and Race, George J, The Effect of Reticulose on Viral Infections of Experimental Animals, Southern Medical Journal, Feb., 1962, 185–188.
Treatment of Viral Diseases with A Lipo–protein Nucleic Acid Complex (Reticulose)—A Clinical Study, Scientific Exhibit: Virginia State Medical Society Meeting, Washington D.C., Nov., 1957.
Kempe, Henry C., Fulginiti, Vincent A., and Vincent, Leone St., Failure to Demonstrate Antiviral Activity of Reticulose, Diseases of Children, vol. 103, No. 5, 655–657, 1962.
Sanders, Murray, Controlled Animal Studies with Reticulose Illustrating of Lipoprotein–Nucleic Acid Complex in the Experimental Animal Infected with Human Pathogenic Viral Entities, Southern Medical Association Scientific Exhibit, Dallas, Texas, Nov., 1961.

*Primary Examiner*—Michael G. Wityshyn
*Assistant Examiner*—Janet M. Kerr
*Attorney, Agent, or Firm*—Cohen, Pontani, Lieberman & Pavane

[57] ABSTRACT

The present invention discloses a method for treating patients having basal cell carcinoma comprising subcutaneous, intralesional or topical administration of Product R, a peptide-nucleic acid preparation.

26 Claims, No Drawings

TREATMENT OF BASAL CELL CARCINOMA WITH PRODUCT R, A PEPTIDE-NUCLEIC ACID PREPARATION

BACKGROUND OF THE INVENTION

I. Field of the Invention

This invention relates to a method of treating basal cell carcinoma with Product R by administering subcutaneously and intralesionally Product R to a patient.

II. Description of the Related Art

Basal cell carcinomas are the most common cutaneous neoplasms found in humans. The majority of the 500,000 new cases of nonmelanoma skin cancers each year are basal cell carcinomas.

Basal cell carcinomas exist in a variety of clinical and histological forms such as nodular-ulcerative, superficial, pigmented, morphealike, fibroepithelioma and nevoid syndrome. Present treatment methods include various surgical techniques such as electrodesiccation and curettage, excision, cryosurgery and irradiation. Cure rates for the surgical techniques are generally stated to be about 95%. Despite the high cure rates effected by surgical techniques, non-surgical methods of therapy are generally thought to be more desirable.

Product R[1] emerged as an antiviral product in the 1930's. While it was originally believed to be a product composed of peptone, peptides and nucleic acids (fully defined hereafter), the precise composition remains unidentified. Nevertheless, Product R has demonstrated an ability to inhibit rapidly the course of several viral diseases. It is nontoxic, miscible with tissue fluids and blood sera and free from anaphylactogenic properties.

1. The agent is known under the trademark "Reticuloses", a trademark of Advanced Viral Research Corp.

Insofar as the applicant knows, Product R has never been used, nor suggested for treatment of basal cell carcinomas.

SUMMARY OF THE INVENTION

An object of this invention therefore is to provide a method for treating a patient having basal cell carcinoma by administering topically, subcutaneously and intralesionally to the patient an effective treatment amount of Product R, a peptide-nucleic acid preparation.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

DETAILED DESCRIPTION OF THE PRESENTLY PREFERRED EMBODIMENTS

As used herein, Product R is the product produced according to either of the following methods.

Method I For Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3 to 7° C. in a suitable container and gently stir until all the ingredients have been properly wet. Carefully add while stirring about 16.5 g of sodium hydroxide (reagent grade ACS) and continue stirring until sodium hydroxide completely dissolved. Autoclave at about 9 lbs pressure and 200–230° F. for a period of time until RNA is completely digested, for example, about 4 hours. At the end of the period, the autoclave is stopped and the reaction flask and contents are permitted to slowly cool to ambient temperature. Then cool for at least six hours at about 3–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/ml, the final volume is approximately 5 liters. The pH is then adjusted with either concentrated HCl (reagent grade ACS) or 1.0 normal NaOH to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclave for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

Method II For Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3 to 7° C. in a suitable container and gently stir until all the ingredients have been properly wet. Slowly add while stirring about 11.75 ml of hydrochloric acid (reagent grade ACS) and continue stirring until hydrochloric acid is completely dissolved. Autoclave at about 9 lbs pressure and 200–230° F. for a period of time until RNA is completely digested, for example, about 4 hours. At the end of the period, the autoclave is stopped and the reaction flask and contents are permitted to slowly cool to ambient temperature. Then cool for at least six hours at about 3–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/ml, the final volume is approximately 5 liters. The pH is then adjusted with either concentrated HCL (reagent grade ACS) or 35% (w/v) of NaOH to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclave for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

According to the present invention, Product R is administered subcutaneously to patients having basal cell carcinoma. A suitable effective dose of Product R is in a range from about 0.5 milliliter to about 2 milliliters, preferably about 1 milliliter, per patient per day. A portion of the effective daily dose may be applied to the location of basal cell carcinoma by injecting above, beneath, or directly into the lesion area, while the balance of the dose is administered to the patient subcutaneously. The size of the lesion area determines the quantity to be injected at the location of the lesion. Generally, a few drops will be sufficient. Preferably, an effective amount of Product R, depending on the size of lesion, may be applied topically to adequately cover the lesion area after the injection. The desired dose may be administered as two, three or more sub-doses at appropriate intervals, generally equally spread in time, throughout the day. Preferably, two sub-doses is administered per day until the lesion area scabs over or is healed completely.

While it is possible for Product R to be administered as part of a pharmaceutical formulation, it is preferable to present it alone, although it may be administered at about the same time as one or more other pharmaceuticals are independently administered. If Product R is administered as part of a pharmaceutical formulation, the formulations of the present invention comprise at least one administered ingredient, as above defined, together with one or more acceptable carriers thereof and optionally other therapeutic ingredients. The carrier(s) must be "acceptable" in the sense of being compatible with the other ingredients of the formulation and not deleterious to the recipient thereof. Preferably, Product R constitutes at least about 90% by weight of such formulations.

The formulations may conveniently be presented in unit-dose or multi-dose containers, e.g. sealed ampules and vials.

Preferred unit dosage formulations are those containing a daily dose or unit, daily sub-dose, or an appropriate fraction of the administered ingredient.

Although these doses and the regimen described were beneficial, it is contemplated that they be considered as only guidelines and that the attending clinician will determine, in his or her judgment, an appropriate dosage and regimen, based on the patient's age and condition as well as the severity of the basal cell carcinoma.

Thus, while there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

The following illustrates the effects of treating patients having basal cell carcinoma with subcutaneously and intralesionally administered Product R.

EXAMPLE

A patient developed an open sore having a size of about 4 or 5 mm×4 or 5 mm from recurring basal cell and sclerosing basal cell carcinomas on the patient's forehead. The patient was treated by injecting subcutaneously 0.5 milliliter of Product R twice a day, and also was injected with a few drops of Product R into and beneath the lesion area. The treatment continued for four days. The inflammation began lessening on the fourth day. Three days after the treatment was stopped, the open sore was reduced to about one fifth of the original size and completely scabbed over.

I claim:

1. A method for treating a patient having basal cell carcinoma, comprising subcutaneously administering an effective treatment amount of Product R in a pharmaceutically injectable formulation to said patient, wherein Product R is made by a process comprising the steps of:
   a. mixing about 35.0 grams of casein, about 17.1 grams of beef peptone, about 22.0 grams of ribonucleic acid (RNA), and about 3.25 grams of bovine serum albumin in about 2.5 liters of water;
   b. adding about 16.5 grams of sodium hydroxide to the mixture from step a;
   c. autoclaving the product from step b at about 9 lbs pressure and 200–300° F. until the RNA is completely digested;
   d. cooling the product from step c to about 3–8° C.;
   e. sequentially filtering the product from step d through a 2 micron filter, a 0.45 micron filter and a 0.2 micron filter;
   f. diluting the product from step e with water to yield a final volume of about 5 liters;
   g. adjusting the pH of the product from step f to a range of about 7.3–7.6;
   h. filtering the product from step g through a second 0.2 micron filter; and
   i. autoclaving the product from step h at 240° F. and 20–30 pounds pressure for about 30 minutes.

2. The method of claim 1, wherein said effective treatment amount of Product R is in a range from about 0.5 to about 2 milliliters per day.

3. The method of claim 1, wherein said effective treatment amount of Product R is about 1 milliliter per day.

4. The method of claim 1, further comprising topically administering an effective treatment amount of Product R to said patient.

5. The method of claim 1, further comprising intralesionally administering an effective treatment amount of Product R to said patient.

6. The method of claim 5, further comprising topically administering an effective treatment amount of Product R to said patient.

7. A method for treating a patient having basal cell carcinoma, comprising intralesionally administering an effective treatment amount of Product R in a pharmaceutically injectable formulation to said patient, wherein Product R is made by a process comprising the steps of:
   a. mixing about 35.0 grams of casein, about 17.1 grams of beef peptone, about 22.0 grams of ribonucleic acid (RNA), and about 3.25 grams of bovine serum albumin in about 2.5 liters of water;
   b. adding about 16.5 grams of sodium hydroxide to the mixture of step a;
   c. autoclaving the product from step b at about 9 lbs pressure and 200–300° F. until the RNA is completely digested;
   d. cooling the product from step c to about 3–8° C.;
   e. sequentially filtering the product from step d through a 2 micron filter, a 0.45 micron filter and a 0.2 micron filter;
   f. diluting the product from step e with water to yield a final volume of about 5 liters;
   g. adjusting the pH of the product from step f to a range of about 7.3–7.6;
   h. filtering the product from step g through a second 0.2 micron filter; and i. autoclaving the product from step h at 240° F. and 20–30 pounds pressure for about 30 minutes.

8. The method of claim 7, wherein said effective treatment amount of Product R is in a range from about 0.5 to about 2 milliliters per day.

9. The method of claim 7, wherein said effective treatment amount of Product R is about 1 milliliter per day.

10. The method of claim 7, further comprising topically administering an effective treatment amount of Product R to said patient.

11. A method for treating a patient having basal cell carcinoma, comprising topically administering an effective treatment amount of Product R in a pharmaceutically acceptable formulation to said patient, wherein Product R is made by a process comprising the steps of:
   a. mixing about 35.0 grams of casein, about 17.1 grams of beef peptone, about 22.0 grams of ribonucleic acid (RNA), and about 3.25 grams of bovine serum albumin in about 2.5 liters of water;
   b. adding about 16.5 grams of sodium hydroxide to the mixture from step a;
   c. autoclaving the product from step b at about 9 lbs pressure and 200–300° F. until the RNA is completely digested;
   d. cooling the product from step c to about 3–8° C.;
   e. sequentially filtering the product from step d through a 2 micron filter, a 0.45 micron filter and a 0.2 micron filter;
   f. diluting the product from step e with water to yield a final volume of about 5 liters;
   g. adjusting the pH of the product from step f to a range of about 7.3–7.6;
   h. filtering the product from step g through a second 0.2 micron filter; and
   i. autoclaving the product from step h at 240° F. and 20–30 pounds pressure for about 30 minutes.

12. The method of claim 11, wherein said effective treatment amount of Product R is in a range from about 0.5 to about 2 milliliters per day.

13. The method of claim 11, wherein said effective treatment amount of Product R is about 1 milliliters per day.

14. A method for treating a patient having basal cell carcinoma, comprising subcutaneously administering an effective treatment amount of Product R in a pharmaceutically injectable formulation to said patient, wherein Product R is made by a process comprising the steps of:
   a. mixing about 35.0 grams of casein, about 17.1 grams of beef peptone, about 22.0 grams of ribonucleic acid (RNA), and about 3.25 grams of bovine serum albumin in about 2.5 liters of water;
   b. adding about 11.75 milliliters of hydrochloric acid to the mixture from step a;
   c. autoclaving the product from step b at about 9 lbs pressure and 200–300° F. until the RNA is completely digested;
   d. cooling the product from step c to about 3–8° C.;
   e. sequentially filtering the product from step d through a 2 micron filter, a 0.45 micron filter and a 0.2 micron filter;
   f. diluting the product from step e with water to yield a final volume of about 5 liters;
   g. adjusting the pH of the product from step f to a range of about 7.3–7.6;
   h. filtering the product from step g through a second 0.2 micron filter; and
   i. autoclaving the product from step h at 240° F. and 20–30 pounds pressure for about 30 minutes.

15. The method of claim 14, wherein said effective treatment amount of Product R is in a range from about 0.5 to about 2 milliliters per day.

16. The method of claim 14, wherein said effective treatment amount of Product R is about 1 milliliter per day.

17. The method of claim 14, further comprising topically administering an effective treatment amount of Product R to said patient.

18. The method of claim 14, further comprising intralesionally administering an effective treatment amount of Product R to said patient.

19. The method of claim 18, further comprising topically administering an effective treatment amount of Product R to said patient.

20. A method for treating a patient having basal cell carcinoma, comprising intralesionally administering an effective treatment amount of Product R in a pharmaceutically injectable formulation to said patient, wherein Product R is made by a process comprising the steps of:
   a. mixing about 35.0 grams of casein, about 17.1 grams of beef peptone, about 22.0 grams of ribonucleic acid (RNA), and about 3.25 grams of bovine serum albumin in about 2.5 liters of water;
   b. adding about 11.75 milliliters of hydrochloric acid to the mixture from step a;
   c. autoclaving the product from step b at about 9 lbs pressure and 200–300° F. until the RNA is completely digested;
   d. cooling the product from step c to about 3–8° C.;
   e. sequentially filtering the product from step d through a 2 micron filter, a 0.45 micron filter and a 0.2 micron filter;
   f. diluting the product from step e with water to yield a final volume of about 5 liters;
   g. adjusting the pH of the product from step f to a range of about 7.3–7.6;
   h. filtering the product from step g through a second 0.2 micron filter; and
   i. autoclaving the product from step h at 240° F. and 20–30 pounds pressure for about 30 minutes.

21. The method of claim 20, wherein said effective treatment amount of Product R is in a range from about 0.5 to about 2 milliliters per day.

22. The method of claim 20, wherein said effective treatment amount of Product R is about 1 milliliter per day.

23. The method of claim 20, further comprising topically administering an effective treatment amount of Product R to said patient.

24. A method for treating a patient having basal cell carcinoma, comprising topically administering an effective treatment amount of Product R in a pharmaceutically acceptable formulation to said patient, wherein Product R is made by a process comprising the steps of:
   a. mixing about 35.0 grams of casein, about 17.1 grams of beef peptone, about 22.0 grams of ribonucleic acid (RNA), and about 3.25 grams of bovine serum albumin in about 2.5 liters of water;
   b. adding about 11.75 milliliters of hydrochloric acid to the mixture from step a;
   c. autoclaving the product from step b at about 9 lbs pressure and 200–300° F. until the RNA is completely digested;
   d. cooling the product from step c to about 3–8° C.;

e. sequentially filtering the product from step d through a 2 micron filter, a 0.45 micron filter and a 0.2 micron filter;

f. diluting the product from step e with water to yield a final volume of about 5 liters;

g. adjusting the pH of the product from step f to a range of about 7.3–7.6;

h. filtering the product from step g through a second 0.2 micron filter; and i. autoclaving the product from step h at 240° F. and 20–30 pounds pressure for about 30 minutes.

25. The method of claim 24, wherein said effective treatment amount of Product R is in a range from about 0.5 to about 2 milliliters per day.

26. The method of claim 24, wherein said effective treatment amount of Product R is about 1 milliliter per day.

* * * * *